United States Patent [19]

Heath, Jr. et al.

[11] Patent Number: 5,441,984

[45] Date of Patent: Aug. 15, 1995

[54] UREA, THIOUREA AND GUANIDINE DERIVATIVES

[75] Inventors: William F. Heath, Jr., Fishers; Jill A. Panetta, Zionsville; John K. Shadle, Fishers, all of Ind.

[73] Assignee: Eli Lilly and Company, Indianapolis, Ind.

[21] Appl. No.: 338,994

[22] Filed: Nov. 14, 1994

Related U.S. Application Data

[63] Continuation of Ser. No. 177,896, Jan. 6, 1994, abandoned.

[51] Int. Cl.⁶ ............... A61K 31/17; A61K 31/155; A61K 31/38; A61K 31/335

[52] U.S. Cl. ................... 514/595; 514/587; 514/585; 514/634; 514/443; 514/469; 514/866; 549/57; 549/58; 549/467; 564/26; 564/28; 564/50; 564/54; 564/52; 564/56; 564/238; 564/239

[58] Field of Search ............ 514/587, 598, 866, 443, 514/469; 549/57, 58, 439, 440, 441; 564/26, 56, 237

[56] References Cited

U.S. PATENT DOCUMENTS

| | | | |
|---|---|---|---|
| 3,004,035 | 10/1961 | Csendes | 564/56 |
| 3,483,296 | 12/1969 | Marlin et al. | 564/49 |
| 3,718,660 | 2/1973 | Plumpe et al. | 260/307 D |
| 3,855,242 | 12/1974 | Chapman et al. | 549/57 |
| 3,953,601 | 4/1976 | Bondesson et al. | 424/275 |
| 4,161,541 | 7/1979 | Rasmussen | 424/326 |
| 4,333,929 | 6/1982 | Cantello | 424/246 |
| 4,465,509 | 8/1984 | Takematsu et al. | 564/56 |
| 4,666,931 | 5/1987 | Ohishi et al. | 514/389 |
| 4,873,259 | 10/1989 | Summers, Jr. et al. | 514/443 |
| 4,959,503 | 9/1990 | Connor et al. | 564/265 |
| 5,015,644 | 5/1991 | Roth et al. | 514/247 |
| 5,023,378 | 6/1991 | Dowle et al. | 564/340 |
| 5,099,030 | 3/1992 | Gardner et al. | 548/478 |
| 5,126,483 | 6/1992 | Sekiya et al. | 564/56 |
| 5,177,259 | 1/1993 | Connor et al. | 562/463 |
| 5,268,500 | 12/1993 | Lalezari et al. | 560/34 |
| 5,296,498 | 3/1994 | Malen et al. | 514/401 |
| 5,373,024 | 12/1994 | Lang et al. | 514/618 |

FOREIGN PATENT DOCUMENTS

| | | |
|---|---|---|
| 0527458 | 2/1993 | European Pat. Off. |
| 2036555 | 7/1980 | United Kingdom |

Primary Examiner—Richard L. Raymond
Assistant Examiner—Deborah Lambkin
Attorney, Agent, or Firm—Martin A. Hay

[57] ABSTRACT

The present invention provides novel urea, thiourea and guanidine derivatives, pharmaceutical formulations thereof and a method of using same to prevent diabetic complications.

18 Claims, No Drawings

UREA, THIOUREA AND GUANIDINE DERIVATIVES

This application is a continuation, of application Ser. No. 08/177,896, filed Jan. 6, 1994, now abandoned.

BACKGROUND OF THE INVENTION

Diabetes mellitus is a systemic disease characterized by disorders in the metabolism of insulin, carbohydrates, fats and proteins, and in the structure and function of blood vessels. The primary symptom of acute diabetes is hyperglycemia, often accompanied by glucosuria, the presence in urine of large amounts of glucose, and polyuria, the excretion of large volumes of urine. Additional complications arise in chronic or long standing diabetes. These complications include degeneration of the walls of blood vessels. Although many different organs are affected by these vascular changes, the eyes, nerves and kidneys appear to be the most susceptible. As such, long standing diabets mellitus, even when treated with insulin, is a leading cause of blindness.

The present invention relates to a series of urea, thiourea and guanidine derivatives which are capable of preventing the development of diabetic complications in mammals. Accordingly, one object of the present invention is to provide compounds having good efficacy in preventing diabetic complications. The compounds of the present invention are also believed to have minimal toxicological or secondary effects. It is, therefore, believed that the compounds of the present invention provide a safe, efficacious way of preventing the development of diabetic complications with a minimum of unwanted side effects. Other objects, features and advantages of the present invention will become apparent from the subsequent description and the appended claims.

SUMMARY OF THE INVENTION

This invention provides compounds of the formula

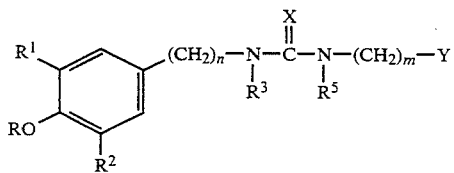

wherein:

R is hydrogen, $C_1-C_8$ alkyl, $C_3-C_8$ cycloalkyl, $C_1-C_6$ alkylphenyl or a hydroxy protecting group;

$R^1$ and $R^2$ are each independently hydrogen, $C_1-C_6$ alkyl, $C_3-C_8$ cycloalky, $C_1-C_6$ alkoxy, $C_2-C_6$ alkenyl, $C_2-C_6$ alkynyl, $-S(O)_q(C_1-C_6$ alkyl) or

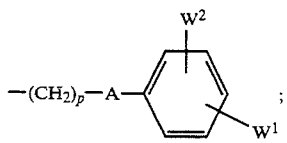

A is $-CH_2-$, $-O-$, $-S-$, $-S(O)-$ or $-S(O)_2-$;
$W^1$ and $W^2$ are each independently hydrogen, halo, hydroxy, $C_1-C_4$ alkyl, $C_1-C_4$ alkoxy, $C_1-C_4$ alkylthio, $C_2-C_4$ alkenyl or $C_2-C_4$ alkynyl;

$R^3$ is hydrogen, $C_1-C_8$ alkyl, $C_3-C_8$ cycloalkyl, or $C_1-C_6$ alkylphenyl;

X is O, S or $NR_4$;

$R^4$ is hydrogen, $C_1-C_6$ alkyl, $C_1-C_4$ alkylphenyl or $C_1-C_6$ alkoxy;

$R^5$ is hydrogen, $C_3-C_8$ cycloalkyl or $C_1-C_8$ alkyl;

Y is

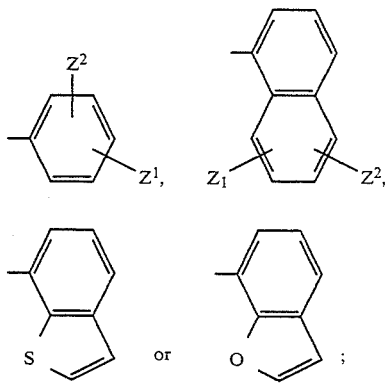

$Z^1$ and $Z^2$ are each independently hydrogen, $C_1-C_6$ alkyl, $C_3-C_8$ cycloalkyl, $C_1-C_6$ alkoxy, hydroxy, $C_2-C_6$ alkenyl, $C_2-C_6$ alkynyl, $C_1-C_6$ alkylthio, halo, trifluoromethyl or $-NR^6R^7$;

$R^6$ and $R^7$ are each independently hydrogenn, $C_3-C_8$ cycloalkyl, $C_1-C_6$ alkyl or $C_1-C_4$ alkylphenyl;

n is 1 to 6, both inclusive;

m and p are each independently 0 to 6, both inclusive;

q is 0, 1 or 2; and pharmaceutically acceptable salts thereof.

The compounds of the above formula are useful for preventing the development of diabetic complications in mammals suffering from diabetes. As such, a further aspect of the present invention is a method of preventing the development of diabetic complications in mammals suffering from diabetes comprising administering to said mammal a therapeutically effective amount of a compound of the formula described above.

Finally, since the compounds of the above formula are useful in preventing the development of diabetic complications in mammals, a final aspect of the present invention provides pharmaceutical compositions comprising as active ingredient a compound as set forth above in association with one or more pharmaceutically acceptable carriers, diluents or excipients therefor.

DETAILED DESCRIPTION OF THE INVENTION

As used herein, the term "$C_1-C_8$ alkyl" represents a straight or branched alkyl chain having from one to eight carbon atoms. Typical $C_1-C_8$ alkyl groups include methyl, ethyl, n-propyl, isopropyl, n-butyl, sec-butyl, isobutyl, t-butyl, n-pentyl, and the like. The term "$C_1-C_8$ alkyl" includes within its definition the terms "$C_1-C_4$ alkyl" and "$C_1-C_6$ alkyl".

"$C_1-C_6$ alkylphenyl" represents a straight or branched chain alkyl group having from one to six carbon atoms attached to a phenyl ring. Typical $C_1-C_6$ alkylphenyl groups include methylphenyl, ethylphenyl, n-propylphenyl, isopropylphenyl, n-butylphenyl, isobutylphenyl, tert-butylphenyl, pentylphenyl and hexylphenyl. The term "$C_1-C_6$ alkylphenyl" includes within its definition the term "$C_1-C_4$ alkylphenyl".

"C₁–C₆ alkoxy" represents a straight or branched alkyl chain having one to six carbon atoms, which chain is attached to the remainder of the molecule by an oxygen atom. Typical $C_1$–$C_6$ alkoxy groups include methoxy, ethoxy, propoxy, isopropoxy, butoxy, isobutoxy, sec-butoxy, tert-butoxy, pentoxy, hexoxy and the like. The term "C₁–C₆ alkoxy" includes within its definition the term "C₁–C₄ alkoxy"

The term "C₂–C₆ alkenyl" refers to straight and branched chain radicals of two to six carbon atoms, both inclusive, having a double bond. As such, the term includes ethylene, propylene, 1-butene, 2-butene, 2-methyl-1-propene, 1pentene, 2-methyl-2-butene and the like. The term "C₂–C₆ alkenyl" includes within its definition the term "C₂–C₄ alkenyl".

The term "C₂–C₆ alkynyl" refers to straight and branched chain radicals of two to six carbon atoms, both inclusive, having a triple bond. As such, the term includes acetylene, propyne, 1-butyne, 2-hexyne, 1-pentyne, 3-ethyl-1-butyne and the like. The term "C₂–C₆ alkynyl" includes within its definition the term "C₂–C₄ alkynyl".

The term "C₃–C₈ cycloalkyl" refers to saturated alicyclic rings of three to eight carbon atoms, both inclusive, such as cyclopropyl, methylcyclopropyl, ethylcyclobutyl, cyclobutyl, cyclopentyl, cyclohexyl, cyclooctyl and the like.

The term "—S(O)q(C₁–C₆ alkyl)" represents a straight or branched alkyl chain having one to six carbon atoms, which chain is attached to the remainder of the molecule by a sulfur (when q is 0), SO (when q is 1) or SO₂ (when q is 2) moiety. Typical —S(O)$_q$(C₁–C₆ alkyl) groups include methylthio, ethylthio, n-propylthio, isopropylthio, n-butylthio, sec-butylthio, t-butylthio, pentylthio-hexylthio and the corresponding sulfone and sulfoxide analogs thereof.

"Halo" represents chloro, bromo, fluoro or iodo.

"C₁–C₆ alkylthio" represents a straight or branched alkyl chain having one to six carbon atoms, which chain in attached to the remainder of the molecule by a sulfur atom. Typical C₁–C₆ alkylthio groups include methylthio, ethylthio, propylthio, butylthio, tert-butylthio, hexylthio and the like. The term "C₁–C₆ althylthio" includes within its definition the term "C₁–C₄ alkylthio".

The term "pharmaceutically acceptable salts" refers to salts of the compounds of the above formula which are substantially non-toxic to living organisms. Typical pharmaceutically acceptable salts include those salts prepared by reaction of the compounds of the above formula with a pharmaceutically acceptable mineral or organic acid, or a pharmaceutically acceptable alkali metal or organic base, depending on the types of substituents present on the compounds of the formula.

Examples of pharmaceutically acceptable mineral acids which may be used to prepare pharmaceutically acceptable salts include hydrochloric acid, phosphoric acid, sulfuric acid, hydrobromic acid, hydroiodic acid, phosphorous acid and the like. Examples of pharmaceutically acceptable organic acids which may be used to prepare pharmaceutically acceptable salts include aliphatic mono and dicarboxylic acids, oxalic acid, carbonic acid, citric acid, succinic acid, phenyl-substituted akanoic acids, aliphatic and aromatic sulfonic acids and the like. Such pharmaceutically acceptable salts prepared from mineral or organic acids thus include hydrochloride, hydrobromide, nitrate, sulfate, pyrosulfate, bisulfate, sulfite, bisulfite, phosphate, monohydro-genphosphate, dihydrogenphosphate, metaphosphate, pyrophosphate, hydroiodide, hydrofluoride, acetate, propionate, formate, oxalate, citrate, lactate, p-toluene-sulfonate, methanesulfonate, maleate, and the like.

Certain of the compounds described above may contain a hydroxy or sulfoxide group. Compounds having such group may be converted to a pharmaceutically acceptable salt by reaction with a pharmaceutically acceptable alkali metal or organic base. Examples of pharmaceutically acceptable organic bases which may be used to prepare pharmaceutically acceptable salts include ammonia, amines such as triethanolamine, triethylamine, ethylamine, and the like. Examples of pharmaceutically acceptable alkali metal bases include compounds of the general formula MOR$^{13}$, where M represents an alkali metal atom, e.g., sodium, potassium, or lithium, and R$^{13}$ represents hydrogen or C₁–C₄ alkyl.

It should be recognized that the particular anion or cation forming a part of any salt of this invention is not critical, so long as the salt, as a whole is pharmacologically acceptable and as long as the anion or cationic moiety does not contribute undesired qualities.

A preferred genus of compounds of the present invention includes those compound wherein R, R$^1$, R$^2$, R$^3$, R$^5$, n, m and Y are as defined above and X is O or S.

Of this preferred genus, those compounds in which n is 1 or 2 (particularly 1) and m is 0, 1 or 2 (particularly 0) are even more preferred.

Of this even more preferred genus, those compounds in which Y is

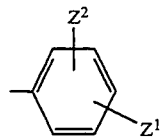

(wherein z$^1$ and z$^2$ are as defined above) are especially preferred.

Of this especially preferred genus, those compounds in which R$^3$ and R$^5$ are each independently hydrogen or methyl (especially hydrogen) are particularly preferred.

Of this particularly preferred genus, those compounds in which R$^1$ and R$^2$ are each independently C₁–C₆ alkyl, C₁–C₆ alkoxy, C₁–C₆ alkylthio or C₁–C₄ alkylthio phenyl are more particularly preferred.

Of this more particularly preferred genus, those compounds in which Y is

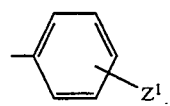

wherein Z$^1$ is hydrogen, C₁–C₄ alkyl, C₁–C₆ alkoxy or C₁–C₆ alkylthio are substantially preferred.

Of this substantially preferred genus, those compounds in which R is hydrogen or C₁–C₄ alkyl are more substantially preferred.

Of this more substantially preferred genus, those compounds in which R is hydrogen or methyl, R$^1$ and R$^2$ each independently n-propyl, isopropyl, n-butyl, sec-butyl, t-butyl, methoxy, ethoxy, methylthio, ethylthio, methyl-thiophenyl or ethylthiophenyl, and Y is

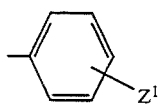

where $Z^1$ is hydrogen, methyl, ethyl, methoxy, ethoxy, methylthio or ethylthio are even more substantially preferred.

The most preferred compounds of the present invention include

N-[[3,5-bis(1,1-dimethylethyl)-4-methoxy phenyl]methyl]-N'-[4-(methylthio)phenyl]urea N-[[3,5-bis(1,1-dimethylethyl)-4-hydroxyphenyl]methyl]-N'-[4-(methylthio)phenyl]urea N-[[3,5-bis(1,1-dimethylethyl)-4-hydroxyphenyl]methyl ]-N'-[2-(methylthio)phenyl]urea N-[[3,5-bis(1,1-dimethylethyl)-4-hydroxyphenyl]methyl ]-N'-phenylurea N-[[3,5-bis(1,1-dimethylethyl)-4-hydroxyphenyl]methyl]-N'-phenylthiourea N-[[3,5-bis(1,1-dimethylethyl)-4-hydroxyphenyl]methyl]-N'-[3-(methylthio)phenyl]urea N-[[3-methylthiophenyl-4-hydroxy-5-(1,1-dimethylethyl)phenyl ]methyl]-N'-[4-(methylthio)phenyl]urea The present invention also encompasses a method of preventing the development of diabetic complications in mammals utilizing a compound of the instant invention, as well as pharmaceutical formulations containing such compounds. Preferred methods and formulations of the present invention are those methods and formulations which contain a preferred compound, or genus of compounds, as described above.

The compounds of the present invention wherein X is S or O can, typically, be prepared by methods well known to one skilled in the art of organic chemistry. For example, such compounds can be prepared by reacting a compound containing an amine moiety with a compound containing a carboxylic acid functionality or an activated derivative thereof. For those compounds of the present invention wherein X is S, the corresponding sulfur containing analog (i.e., C=S in place of C=O) of the carboxylic acid or activated derivative thereof will, of course, be employed. Such reaction is illustrated in the following reaction schemes.

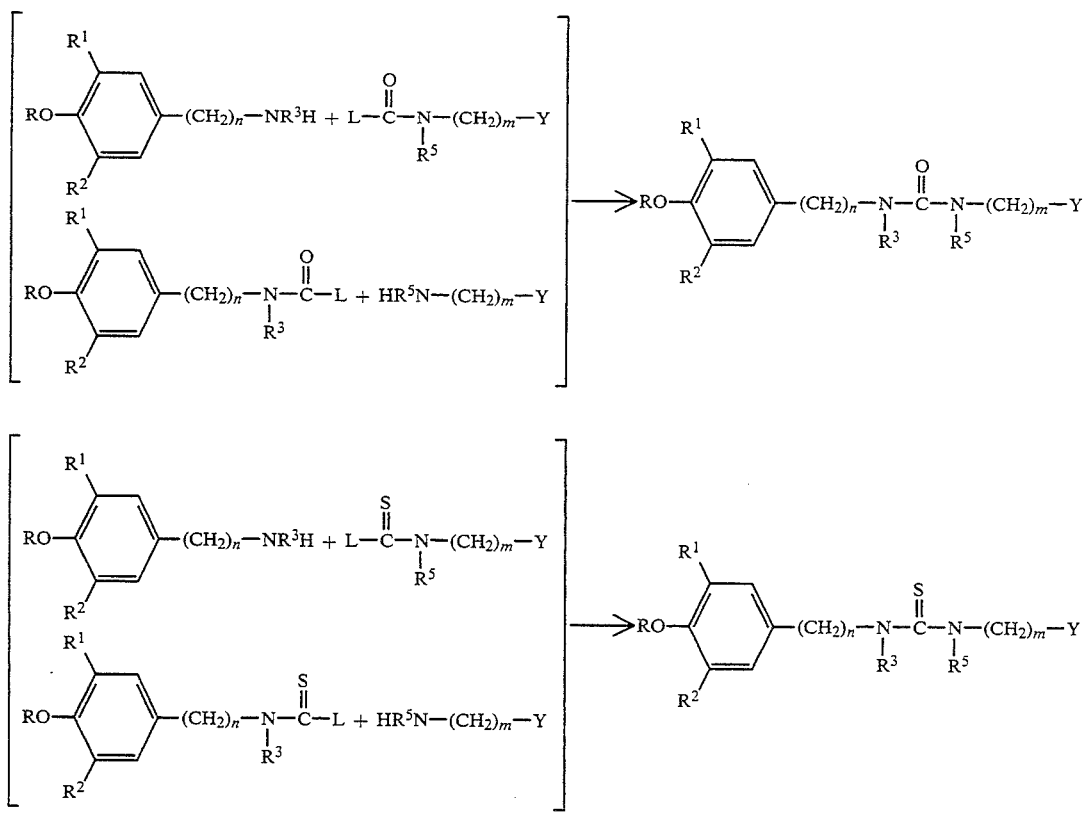

where R, $R^1$, $R^2$, $R^3$, $R^5$ n m and Y are as defined above and the C(O)L or C(S)L moiety comprises a carboxylic acid, amide, acyl halide, ester or anhydride (or a sulfur containing analog thereof) functionality. In many cases the reaction described above is preferably carried out in an acidic solution (such as an acetic acid solution) in order to increase the reactivity of the carboylic acid (or activated derivative thereof) substrate. Further, when a compound containing a carboxylic acid functionality is employed as a substrate a coupling reagent such as dicyclohexylcarbodiimide or diimidazolylcarbonyl is also preferably employed in order to increase reaction rate.

Alternatively, compounds of the present invention wherein X is S or O can be prepared by reacting a compound containing an amine moiety with a compound containing an isocyanate or thioisocyanate substituent, or by cleaving an $\alpha,\beta$-acetylenic amide with an amine. Such reactions are illustrated, for those compounds wherein X is O, by the following reaction schemes.

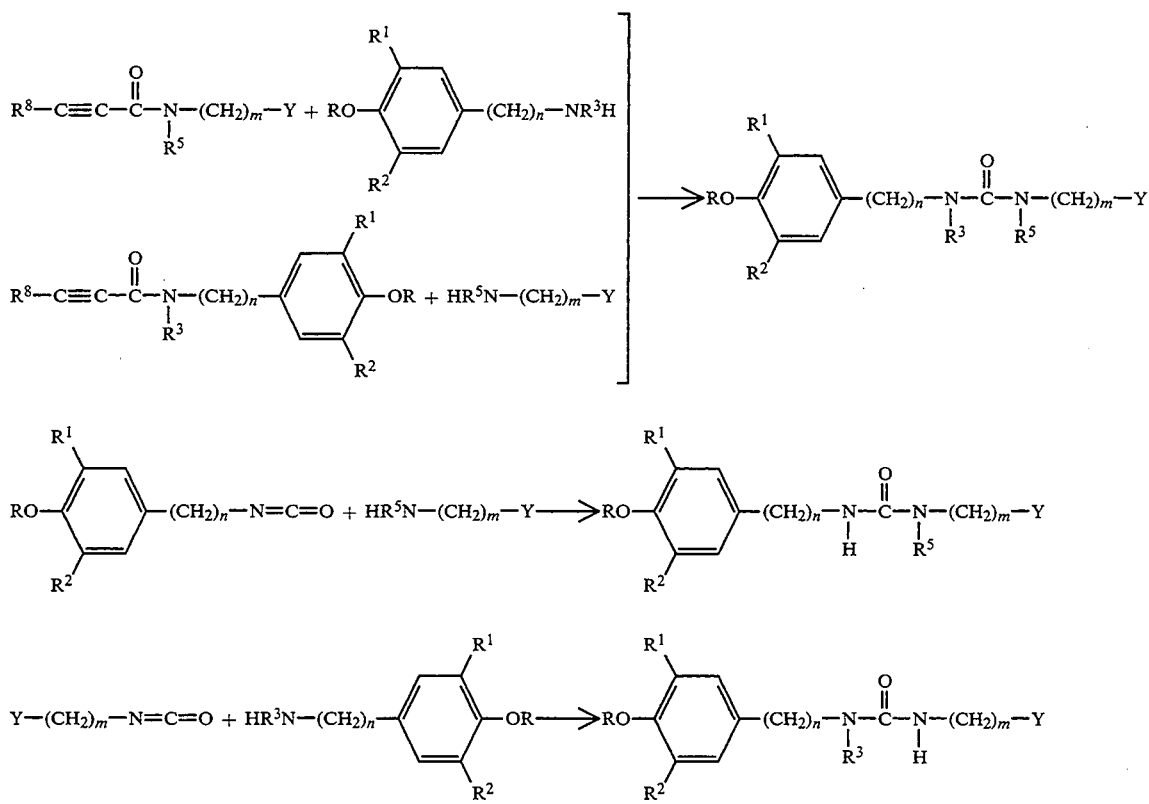

In the above reaction schemes R, R$^1$, R$^2$, R$^3$, R$^5$, m, n and Y are as defined above, while R$^8$ is C$_1$-C$_8$ alkyl, phenyl or C$_1$-C$_6$ alkylphenyl. Obviously, compounds wherein X is S can be prepared in an analogous manner employing substrates where in the carbonyl moiety has been replaced by a thiocarbonyl group.

Compounds of the present invention wherein X is NR$^4$ can also be prepared by methods well known to one skilled in the art. For example, such compounds can be prepared by reacting a compound containing an amine functionality with an alkylthio pseudourea as follows:

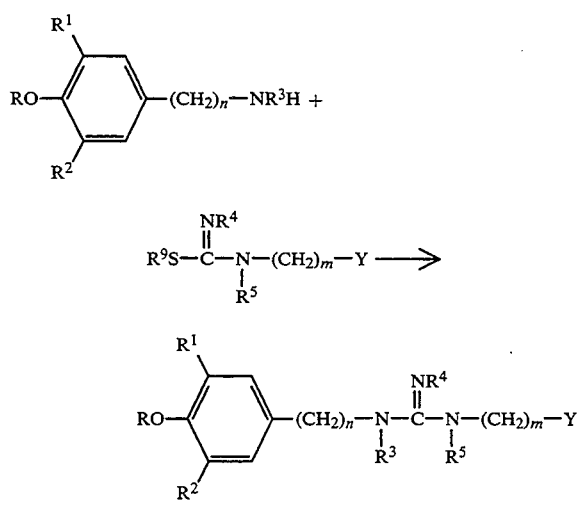

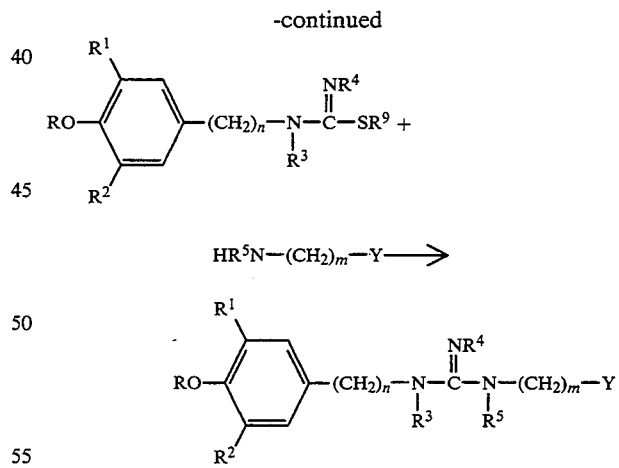

where R, R$^1$, R$^2$, R$^3$, R$^4$, R$^5$, n, m and Y are as defined above and R$^9$ is C$_1$-C$_6$ alkyl. Of course, one could also use the corresponding alkoxy pseudourea (i.e., OR$^9$ in place of SR$^9$) in both of the above reactions as well.

Alternatively, compounds of the present invention wherein x is NR$^4$ can be prepared from the corresponding urea (X is O) and thiourea (X is S) compounds of the present invention. Such reaction entails reacting a urea or thiourea compound of the present invention with an amine of the formula H$_2$NR$^4$. Such reaction is illustrated, using a urea substrate for exemplification purposes only, as follows:

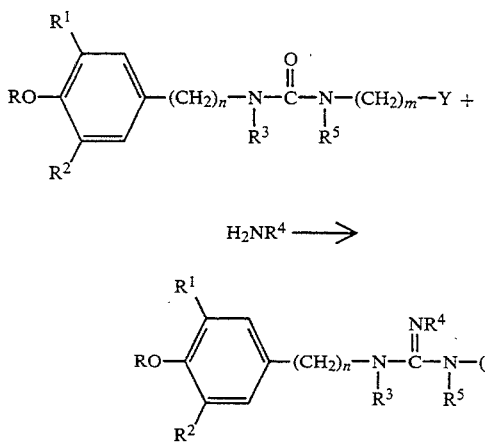

where R, $R^1$, $R^2$, $R^3$, $R^4$, $R^5$, n, m and Y are as defined above.

Those compounds where $R^1$ and $R^2$ are each independently $-S(O)q(C_1-C_6$ alkyl$)$ or

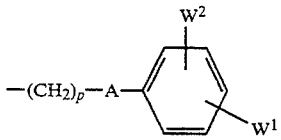

where q is 1 or 2 and A is SO or $SO_2$ are readily prepared from their thiol analogs by treatment with an oxidizing agent, such as m-chloro-perbenzoic acid, in an appropriate organic solvent, such as chloroform, for a time sufficient to effect the desired oxidation.

Compounds wherein R is $C_1-C_8$ alkyl, $C_3-C_8$ cycloalkyl or $C_1-C_6$ alkylphenyl can be prepared by using an appropriately substituted substrate per one of the reaction schemes described above. Alternatively, such compounds can be prepared from the corresponding compound wherein R is hydrogen by reaction with a diazo compound of the formula $(R^{10})_2CH_2$, where each $R^{10}$ is chosen so as to ultimately provide an R substituent in the final product compound which is $C_1-C_8$ alkyl, $C_3-C_8$ cycloalkyl or $C_1-C_6$ alkylphenyl. Furthermore, the corresponding compound wherein R is hydrogen can be reacted with RX (where R is $C_1-C_8$ alkyl, $C_3-C_8$ cycloalkyl or $C_1-C_6$ alkylphenyl and X is halo) in the presence of a base so as to provide compounds of the present invention wherein R is $C_1-C_8$ alkyl, $C_3-C_8$ cycloalkyl or $C_1-C_6$ alkylphenyl.

The compounds of the present invention include various substituents at several positions of the molecule. Such substituted compounds are typically prepared by using an appropriately substituted starting material according to one of the reaction schemes described above. However, in certain cases it may advantageous to convert one type of substituent to another after the base molecule has been assembled. Such substituent conversion is readily accomplished using reactions well known to one versed in synthetic organic chemistry.

Furthermore, in certain instances it may be advisable to protect the hydroxy groups which can be present at various positions of the compounds of the present invention (and, in particular, the hydroxy group present when R is hydrogen) in order to keep such groups from participating in undesired reactions or from being decomposed in some matter. The protecting groups used in such case are chosen from the groups commonly used in synthetic organic chemistry for such purpose. Chemists are accustomed to choosing groups which can be efficiently placed on a hydroxy group and which can also be easily removed when the reaction is complete. Suitable groups are described in standard textbooks, such as Chapter 3 of *Protective Groups in Organic Chemistry*, McOmie, ed. Plenum Press, N.Y. (1973) and Chapter 2 of *Protective Groups in Organic Synthesis*, Greene, John Wiley and Sons, N.Y. (1981).

The hydroxy protected compounds described above, while having activity in preventing the development of diabetic complications in and of themselves, are generally useful as intermediates to the non-hydroxy protected pharmaceutically active compounds of the present invention. Being intermediates, the hydroxy protecting group is removed once its presence is no longer required. Removal of such protecting group is accomplished using techniques extremely familiar to the artisan.

It will be readily appreciated by one skilled in the art that the various substrates required for the reactions described above are either commercially available or may be readily prepared by known techniques from commercially available starting materials. For example, amine reactants of the formula

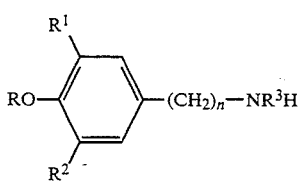

may be prepared according to the following reaction scheme

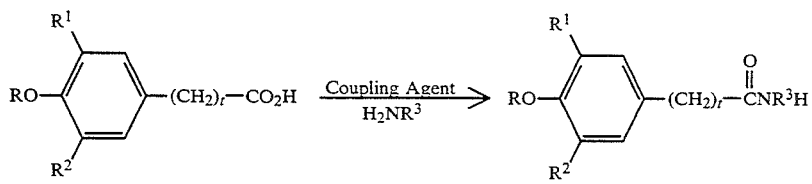

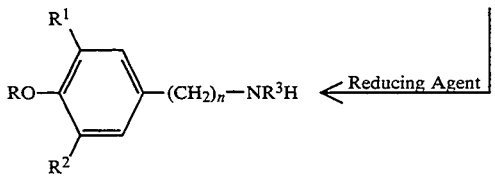

wherein R, R¹, R², R³ and n are as defined above and t is 1–5. Likewise, compounds containing an amide functionality (an activated derivative of a carboxylic acid functionality) of the formula

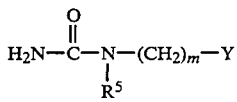

may be prepared according to the following reaction scheme

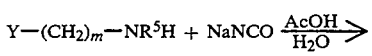

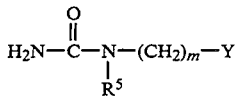

wherein Y, m and R⁵ are as defined above.

The following examples further illustrate the preparation of the compounds of this invention. The examples are illustrative only and are not intended to limit the scope of the invention in any way.

EXAMPLE 1

3,5-Bis(1,1-dimethylethyl)-4-(methoxymethoxy)benzylamine

A. 2,6-Bis(1,1-dimethylethyl)-4-carboxamido-phenol

To 25 g (100 mmol) of 3,5-bis(1,1-dimethylethyl)-4-hydroxy benzoic acid dissolved in 400 ml of tetrahydrofuran were added 17.82 g (110 mmol) of carbonyldiimidazole. The resulting solution was stirred at reflux temperature for three hours and then cooled to room temperature. Once cool, 100 ml of ammonia were added. The resulting solution was stirred for 16 hours and then diluted with water. The dilute solution was then acidified to a pH of 5.5 with a 1N hydrochloric acid solution. The above-titled product crystallized and 24.74 g were recovered by filtration, mp 260°–265° C.

B. 3,5-Bis(1,1-dimethylethyl)-4-(methoxymethoxy)-benzamide

A portion of the compound prepared in (A) above (18.2 g; 73.1 mmol) was dissolved in 385 ml of a 10/1 tetrahydrofuran/dimethylformamide solution. Once dissolution was complete, 2.92 g of a sodium hydride dispersion (60% by weight, sodium hydride dispersed in mineral oil) were slowly added over a period of 5 minutes. The resulting solution was then stirred for 30 minutes. After stirring for 30 minutes, 5.88 g (73.1 mmol) of methoxymethylchloride were added and the resulting solution was stirred for 6 hours. An ethylacetate/water mixture was then added to the reaction solution and the resulting mixture was allowed to separate into an aqueous and an organic phase. The organic phase was isolated, washed eight times with a 1 N sodium hydroxide solution, once with water, and, finally, once with a saturated brine solution. The resulting purified solution was then concentrated to dryness in vacuo to provide 19.5 g of a solid which assayed by NMR as 4.4/1 product/starting material. This impure solid was then purified by recrystallization from methanol/water to provide 14.04 g of a solid, which solid was then recrystallized from a hexane/methylene chloride/chloroform mixture to give 10.94 g of a solid which assayed by NMR as 4/1 title compound/starting material.

The aqueous phase remaining after isolation of the original organic phase was acidified with a 1N hydrochloric acid solution. Solids which precipitated were recovered by filtration and crystallized from chloroform/methanol to give 2.47 g of starting phenol. All organic filtrates were combined and the resulting solution was concentrated until solids precipitated. These solids were recovered by filtration and washed with water to provide 14.8 g of title product.

C. 3,5-Bis(dimethylethyl)-4-(methoxymethoxy)benzylamine

To a solution of 10.9 g (37.2 mmol) of the compound prepared in B) above dissolved in 400 ml of tetrahydrofuran were added 2.12 g (55.7 mmol) of lithium aluminum hydride (slowly over a period of 7 minutes). The resulting solution was stirred at reflux temperature for 3.5 hours and then cooled to room temperature. Once cool, 2.2 ml of water were added followed by the addition of 2.2 ml of a 15% (by weight) solution of sodium hydroxide in water and then another 6.6 ml of water. The resulting precipitate was removed by filtration and then the filtrate was concentrated to dryness in vacuo to provide 11.11 g of compound which assayed by NMR as essentially pure title compound.

EXAMPLE 2

3,5-Bis(1,1-dimethylethyl)-4-(methoxy)benzylamine

A. 3,5-Bis(1,1-dimethylethyl)-4-methoxy-benzoic acid

To 50 g (200 mmol) of 3,5-bis(1,1-dimethylethyl)-4-hydroxy benzoic acid dissolved in 1.1 liters of a 10/1 tetrahydrofuran/dimethylformamide solution were added 24.0 g of a sodium hydride dispersion (60%, by weight, sodium hydride dispersed in mineral oil). The sodium hydride dispersion was added portionwise at a rate such that the reaction solution temperature was kept below 35° C. The resulting solution was stirred for 19 hours and then 28.4 g (220 mmol) of methyl iodide were added. The resulting solution was stirred for 22 hours and then 25 ml of water were added to quench the reaction. Four hundred milliliters of a 1N hydrochloric acid solution were then added in order to acidify the quenched solution. The acidic solution was then concentrated and extracted three times with ethyl acetate. The ethyl acetate extracts were combined, washed three times with water and once with a saturated brine solution and then concentrated to dryness to provide residue. This residue was crystallized from a hexane/- methylene chloride solution to provide 34.62 of title product m.p. 192°–195° C.

B. 3,5-Bis(1,1-dimethylethyl)-4-(methoxy)-benzamide

In a manner analogous to that described in Example 1A above, 34.6 g (131 mmol) of the compound prepared in Example 2A were reacted with 23.37 g (144 mmol) of carbonyldiimidazole and 135 ml of ammonia to produce 35.07 g of title product. m.p. 239°–243° C.

C. 3.5-Bis(1,1-dimethylethyl)-4-(methoxy)benzylamine

In a manner analogous to that described in Example 1C, above, 35.0 g (133 mmol) of the compound prepared in Example 2B were reacted with 7.6 g (200 mmol) of lithium aluminum hydride to provide, after concentration of the filtrate to dryness, 32.0 g of a residue. This residue was dissolved in 600 ml of diethyl ether, after which hydrochloric acid gas was bubbled through the solution. The resulting precipitate was recovered by filtration and then recrystallized from a hexane/isopropanol solution to provide 6.17 g of title compound as the hydrochloride salt. m.p. 250° C.

EXAMPLE 3

3-(Methylthiophenyl)-4-(methoxymethoxy)-5-(1,1-dimethylethyl)benzylamine

A. O-Allyl-2-(1,1-dimethylethyl)phenol

A solution of 150 g (1 mol) of 2-(1,1-dimethylethyl)-phenol, 151.8 g (1.1. mol) of potassium carbonate and 115 g (1.05 mol) of allyl bromide dissolved in 500 ml of acetone was stirred at reflux temperature for 70 hours and then cooled to room temperature. Once cooled, all precipitates were removed by filtration and the resulting filtrate was concentrated to provide a residue. This residue was dissolved in ethyl acetate and the resulting solution was washed with a 1 N hydrochloric acid solution, water and then a saturated brine solution and then concentrated to dryness to provide a residue. This residue was purified by column chromatography, using hexane as eluent, to provide 167.1 g of title compound.

B. 3-(1,1-Dimethylethyl)-4-(allyloxy)-benzaldehyde

To cold (2° C.) N-methylformanilide (197 g; 1.46 mol) were added, over 15 minutes, 208.6 g (1.36 mol) of phosphorus oxychloride. The resulting solution was stirred for 30 minutes and then 167.1 g (879.5 mmol) of the compound of Example 3A were added over a period of 25 minutes. Once all of the compound of Example 3A had been added the resulting solution was heated to 70° C. The reaction exothermed to 110° C. and there was much bubbling. The reaction was cooled to 70° C. and stirred at that temperature for 2 hours. After two hours 200 ml of chloroform were added and the resulting solution was chilled to 15° C. Cold (5° C.) water was then added to quench the reaction (at a rate such that the resulting mixture's temperature did not exceed 45° C.). Once all of the water had been added, and the mixture had cooled back to room temperature, the pH of the mixture was adjusted to pH 5.0 by adding potassium carbonate. The organic phase of the two-phase mixture was then separated from the liquid phase, washed five times with water and then concentrated to provide a residue. This residue was purified by column chromatography, using chloroform as eluent. Fractions containing the title compound were combined, concentrated and then washed with a 1 N hydrochloric acid solution and water. These washed fractions were then concentrated to dryness to provide a residue. Further column chromatography of this residue ultimately provided 128.0 g of pure title compound.

C. 3-(1,1-Dimethylethyl)-4-hydroxy-benzaldehyde

A portion of the compound prepared in Example 3B, above, (58.62 g; 268.9 mmol), palladium (II) acetate (6.0 g; 26.89 mmol), triphenylphosphine (42.27 g; 161.3 mmol) and formic acid (13.6 g; 295.8 mmol) were mixed together in a 1-liter 3-necked round bottom flask. Once all ingredients were mixed, the flask was immersed, while stirring under nitrogen, in a 75° C. oil bath for two minutes. An energetic evolution of gas occurred. After two minutes, the flask was removed from the bath and the contents of the flask were allowed to cool to room temperature. Once the reaction mixture was cooled to room temperature ethyl acetate was added. The resulting solution was washed with a saturated sodium bicarbonate solution, water and then a saturated brine solution. The washed solution was then concentrated to dryness to provide a residue which was, in turn, purified using column chromatography (chloroform for 10 minutes, followed by a 0-10% acetone in chloroform gradient for 10 minutes, as eluent). Fractions containing the desired title compound were combined and then concentrated to dryness to provide a residue. This residue was recrystallized from hexane/methylene chloride. The recrystallized solid was further purified by column chromatography (chloroform eluent) followed by recrystallization from a hexane/methylene chloride/acetone solution to provide 35.8 g of title compound.

D. 3-(Methylthiophenyl)-4-(hydroxy)-5-(1,1-dimethylethyl)benzaldehyde

To a solution of 35.5 g (199 mmol) of the compound prepared in Example 3C, above, thiophenol (24.1 g; 219 mmol) and 70.9 ml of a 40% (weight percent) formaldehyde solution dissolved in 300 ml of 2-ethoxyethanol were added 7.98 g (199 mmol) of sodium hydroxide. The resulting solution was stirred at reflux temperature for 3.5 hours and then cooled to room temperature. Five hundred milliliters of ethyl acetate were then added and the resulting solution was washed once with a 1N hydrochloric acid solution and twice with water. The washed organic solution was filtered to remove any solid particulates and then washed again with water and a saturated brine solution. The resulting solution was concentrated to dryness to provide 59.4 g of a residue. This residue was purified using column chromatography (pure toluene for 15 minutes, followed by a 0-15% ethyl acetate in toluene gradient, as eluent). Fractions containing title compound were combined and then concentrated to dryness to provide a residue. This residue was dissolved in toluene containing a trace of hexane and the resulting solution was chromatographed using toluene as eluent. Fractions containing title compound were, once again, combined and then concentrated to dryness to provide 12.81 g of title product.

E. 3-(Methylthiophenyl)-4-(methoxymethoxy)-5-(1,1-dimethylethyl)benzaldehyde

In a manner analogous to that described in Example 1B, 16.4 g (54.7 mmol) of the compound prepared in Example 3D, above, 3.28 g of a 60% sodium hydride dispersion (60%, by weight, sodium hydride dispersed in mineral oil) and 5.49 g (68.3 mmol) of methoxymethyl-chloride were reacted in order to provide 22.6 g of title compound.

F. 3-(Methylthiophenyl)-4-(methoxymethoxy)-5-(1,1-dimethylethyl)benzoxime

To a portion of the compound produced in Example 3E, above, (20 g; 58 mmol) dissolved in 200 ml of ethanol were added 4.8 g (70 mmol) of hydroxylamine hydrochloride and 35 ml of a 2N sodium hydroxide solution. Most of the hydroxylamine hydrochloride material went into solution and the resulting mixture was then stirred for 2 hours at room temperature. After stirring for two hours the mixture was concentrated to dryness to provide a residue, which residue was then dissolved in ethyl acetate. The resulting solution was washed three times with water [giving one slightly basic solution (pH 9.0), one neutral solution and one slightly acidic solution (pH 5.0)] and then a saturated brine solution. The washed solution was dried over sodium sulfate and then concentrated to dryness to provide a residue. This residue was purified by column chromatography (0–25% ethyl acetate in hexane gradient as eluent) to provide fractions which contained title compound. These fractions were combined and then concentrated to dryness to provide 5.82 g of title compound.

G. 3-(Methylthiophenyl)-4-(methoxymethoxy)-5-(1,1-dimethylethyl)benzylamine.

The compound produced in Example 3F, above, (5.82 g; 16.2 mmol) was dissolved in 160 ml of tetrahydrofuran. Once dissolved, 24.34 ml of a 1.0M lithium aluminum hydride in tetrahydrofuran solution were added over a period of two minutes and the resulting solution was stirred for 8 hours. Water (0.95 ml) was then slowly added to quench the reaction, followed by the addition of 0.95 ml of a 15% (weight percent) aqueous sodium hydroxide solution and then 2.85 ml of water. All precipitated material was removed by filtration and the resulting filtrate was concentrated to dryness to provide a residue. This residue was then dissolved in ethyl acetate and the resulting solution was washed twice with water, once with a saturated brine solution and then dried over sodium sulfate. The dried solution was concentrated to dryness to provide 4.51 g of title compound.

EXAMPLE 4

N-[3,5-Bis(1,1-dimethylethyl)-4-hydroxyphenyl]urea

A. 2,6-Bis(1,1-dimethylethyl)-4-nitrosophenol

To a solution of 2,6-bis(1,1-dimethylethyl)-phenol (229.7 g; 1.11 mol) dissolved in 2750 ml of ethanol were added 590 ml of concentrated hydrochloric acid. The resulting solution was cooled to 5° C. and 114.9 g (1.665 mol) of sodium nitrite were added over a period of approximately 45 minutes. The resulting solution was allowed to warm to room temperature and then stirred for 90 minutes at that temperature. After stirring for 90 minutes, all precipitated matter was removed by filtration and then partially dissolved in chloroform. Any solid particulates which did not dissolve in chloroform were removed by filtration and the resulting filtrate was then concentrated to dryness to provide 13.8 g of a residue.

The filtrate from the initial filtration was concentrated until solids precipitated. These solids were recovered by filtration and then added to a ½ chloroform/hexane solution. Solid particulates which did not dissolve in the chloroform/hexane solution were isolated by filtration to provide 36.7 g of title compound. The filtrate from this filtration was combined with the 13.8 g of residue obtained above and the resulting solution was further concentrated until solids precipitated. These solids were recovered by filtration to provide an additional 7.5 g of title compound. The liltrate from this latest filtration was chromatographed using chloroform as eluent to provide fractions containing title product. These fractions were combined and then concentrated to dryness to provide yet an additional 3.6 g of title product. All title product isolated was combined to provide a total of 47.8 g of title product.

B. 2,6-Bis(1,1-dimethylethyl)-4-aminophenol

The material prepared in Example 4B, above, was combined with an additional 18.1 g of 2,6-bis(1,1-dimethylethyl)-4-nitrosophenol produced in substantially the same way as described in Example 4B to provide a total amount of 65.9 g (280 mmol) of the nitrosophenol compound. This material was then dissolved in 300 ml of ethanol and 83.7 g of animal charcoal and 28 g (560 mmol) of hydrazine monohydrate were added. The resulting mixture was heated to reflux, stirred at that temperature for 2 hours and then cooled to room temperature. Once cool, all solid particulates were removed by filtration through a Hi-Flo filter pad. The filtrate was then concentrated to dryness to provide 64.9 g of impure title product. The material was purified by trituration with hexane to provide 56.3 g of essentially pure title compound.

C. N-[3,5-Bis(1,1-dimethylethyl)-4-hydroxyphenyl]urea

A portion of the compound prepared in Example 4B, above, (25 g; 113 mmol) was suspended in a solution consisting of 56 ml of acetic acid, 113 ml of water and 113 ml of a 1N hydrochloric acid solution. This suspension was then added to a solution of 14.7 g (226 mmol) of sodium cyanate dissolved in 113 ml of water. The resulting suspension was stirred for 3 hours at room temperature and then filtered to provide 24.1 g of impure title compound. This impure product was purified by trituration with hexane to provide 18.14 g of essentially pure title compound.

EXAMPLE 5

N-(4-methylthiophenyl)urea

A solution of 30 g (170 mmol) of 4-(methylmercapto)aniline dissolved in 83 ml of acetic acid and 165 ml of water was heated to 40° C. Once warmed to 40° C. a solution of sodium cyanate (22.2 g; 340 mmol) in 150 ml of water was slowly added. The resulting suspension was stirred for 15 minutes and then allowed to sit for 2 hours. Filtration of the suspension provided 29.98 g of title compound. m.p. 155°–159° C.

EXAMPLE 6

N-[[3,5-Bis(1,1-dimethylethyl)-4-hydroxyphenyl]methyl]-N'-[4-(methylthio)phenyl]urea A. N-[[3,5-Bis(1,1-dimethylethyl)-4-methoxymethoxyphenyl]methyl]-N'-[4-(methylthio)phenyl]urea Acetic acid (1.08 g; 18 mmol), 4.5 g (24.7 mmol) of the compound of Example 5 and 5.0 g (18 mmol) of the compound of Example 1 were dissolved in 180 ml of toluene. The resulting solution was heated to reflux, stirred at that temperature for 4 hours and then cooled to room temperature. The cooled solution was washed with a 1N hydrochloric acid solution, a saturated sodium bicarbonate solution, water and a saturated brine solution. The washed solution was then filtered to remove any solid particulates which had formed and the liltrate was concentrated to dryness to provide a residue. This residue was purified by column chromatography using a 20–40% ethyl acetate in hexane gradient as eluent. Fractions containing the above titled compound were combined and then concentrated to dryness to provide 3.14 g of title compound.

B. N-[[3,5-Bis(1,1-dimethylethyl)-4-hydroxyphenyl]-methyl]-N'-[4-(methylthio)phenyl]urea The compound prepared in Example 6A, above, (2.9 g; 6.5 mmol) was dissolved in 200 ml of tetrahydrofuran. Once dissolved, 50 ml of a 1N hydrochloric acid solution were added and the resulting solution was heated to reflux, stirred at that temperature for one hour, cooled to room temperature and then stirred at that temperature for two hours. NMR analysis of the reaction solution indicated very little reaction had occurred, so another 25 ml of a 1N hydrochloric acid solution were added and the resulting solution was heated to reflux and stirred at that temperature for 8 hours. After this additional stirring time, the reaction solution was concentrated to dryness to provide a residue which was dried in vacuo overnight. This residue was purified by recrystallization from a hexane/methylene chloride solution to provide 2.0 g of title compound. m.p. 141°–145° C.

NMR (CDCl$_3$): $\delta = 1.39$ (s, 18H); 2.42 (s, 3H); 4.35 (s, 2H); 7.11 (s, 2H); 7.23 (s, 4H)

Analysis for C$_{23}$H$_{32}$N$_2$O$_2$S:
Calculated: C, 68.96; H, 8.05; N, 6.99;
Found: C, 68.66; H, 7.97, N, 7.15

EXAMPLE 7

N-[[3,5-Bis(1,1-dimethylethyl)-4-methoxyphenyl]methyl]-N'-(4-methylthio)phenyl]urea The above-titled compound was prepared substantially in accordance with the procedure described in Example 6A, above, using 9.68 g (53.2 mmol) of 3,5-bis(1,1-dimethylethyl)-4-(methoxy)benzylamine (prepared substantially in accordance with the procedure described in Example 2), 13.24 g (53.2 mmol) of the compound of Example 5, 3.19 g (53.2 mmol) of acetic acid and ml of toluene. Such reaction provided 22.02 g of the above-titled compound m.p. 145°–148° C.

NMR (CDCL$_3$): $\delta = 1.39$ (s, 18H); 2.42 (s, 3H); 3.65 (s, 3 H); 4.27 (d, 2H); 6.98–7.15 (m, 6H)

Analysis for C$_{24}$H$_{34}$N$_2$O$_2$S:
Calculated: C, 69.53; H, 8.26; N, 6.76;
Found: C, 69.77; H, 8.29; N, 6.93

EXAMPLE 8

N-[[3,5-Bis(1,1-dimethylethyl)-4-hydroxyphenyl]methyl]-N'-phenyl]urea

The above-titled compound was prepared substantially in accordance with the procedure described in Example 6A using 5.4 g (19.2 mmol) of 3,5-Bis(1,1-dimethylethyl)-4-(methoxymethoxy) benzylamine (prepared substantially in accordance with the procedures described in Example 1), 2.61 g (19.2 mmol) of N-phenylurea, 0.96 g (16 mmol) of acetic acid and 160 ml of toluene. Such reaction provided 700 g of N-[[3,5-bis-(1,1-dimethylethyl)-4-(methoxymethoxy)phenyl]methyl]-N'-phenylurea. (m.p. 168°–170° C.). The methoxymethyl hydroxy protecting group was then removed, substantially in accordance with the procedure described in Example 6B, to provide 600 mg of the above-titled compound. m.p. 199°–202° C.

NMR(CDCl$_3$): $\delta = 1.30$ (s, 18H); 4.17 (s, 2H); 6.80–7.29 (m, 7H)

Analysis for C$_{22}$H$_{30}$N$_2$O$_2$:
Calculated: C, 74.54; H, 8.53; N, 7.90;
Found: C, 74.32; H, 8.57; N, 8.10.

EXAMPLE 9

N-[[3,5-Bis(1,1-dimethylethyl)-4-hydroxyphenyl]methyl]-N'-[2-(methylthio)phenyl]urea The above-titled compound was prepared substantially in accordance with the procedure described in Example 6A using 5.2 g (18.5 mmol) of 3,5-bis(1,1-dimethylethyl)-4-(methoxymethoxy)benzylamine (prepared substantially in accordance with the procedures described in Example 1), 4.6 g (25.4 mmol) of N-2-(methylthio)phenyl]urea (prepared substantially in accordance with the procedures set forth in Example 5), 1.06 ml of acetic acid and 180 ml of toluene. Such reaction provided 1.15 g of N-[[3,5-bis(1,1-dimethylethyl) -4-(methoxymethoxy) phenyl]methyl]-N'-[2-(methylthio)-phenyl]-urea. The methoxymethyl hydroxy protecting group was then removed, substantially in accordance with the procedure described in Example 6B, to provide 740 mg of title compound. m.p. 150°–155° C.

NMR (CDCl$_3$) $\delta = 1.43$ (s, 18H); 2.33 (s, 3H); 4.42 (s, 2H); 7.00–7.95 (m, 6H) .

Analysis for C$_{23}$H$_{32}$N$_2$O$_2$S:
Calculated: C, 68.96; H, 8.05; N, 6.99;
Found: C, 68.96; H, 8.12; N, 7.24

EXAMPLE 10

N-[[3,5-Bis(1,1-dimethylethyl)-4-hydroxyphenyl]methyl]-N'-phenylthiourea

The above-titled compound was prepared substantially in accordance with the procedure described in Example 6A using 5.2 g (18.5 mmol) of 3,5-bis(1,1-dimethylethyl)-4-(methoxymethoxy) benzylamine (prepared substantially in accordance with the procedures described in Example 1), 3.86 g (25.4 mmol) of N-phenylthiourea, 1.11 g (18.5 mol) of acetic acid and 180 ml of toluene. Such reaction provided 4.55 g of N[[3,5-bis(1,1-dimethylethyl)-4-(methoxymethoxy]phenyl]methyl]-N'-phenylthiourea. The methoxymethyl hydroxy protecting group was then removed, substantially in accordance with the procedure described in Example 6B, to provide 790 mg of title compound. m.p. 176°–179° C.

NMR (CDCl$_3$): $\delta = 1.43$ (s, 18H); 4.77 (s, 2H); 5.22 (s, 1H); 6.20 (bs, 1H); 7.08–7.41 (m, 7H); 7.45 (bs, 1H) .

Analysis for C$_{22}$H$_{30}$N$_2$OS:
Calculated: C, 71.31; H, 8.16; N, 7.56;
Found: C, 71.30; H, 7.92; N, 7.43.

EXAMPLE 11

N-[[3,5-Bis(1,1-dimethylethyl)-4-hydroxyphenyl]methyl]-N'-[3-(methylthio)phenyl]urea The above-titled compound was prepared substantially in accordance with the procedure described in Example 6A using 5.2 g (18.5 mmol of 3,5-bis(1,1-dimethylethyl)-4-(methoxymethoxy)benzylamine, 4.62 g (25.4 mmol) of N-[3(methylthio) phenyl]urea (prepared substantially in accordance with the procedure described in Example 5), 1.06 ml of acetic acid and 180 ml of toluene. Such reaction provided 2.06 g of N[[3,5-bis(1,1-dimethylethyl)-4-(methoxymethoxy)phenyl]methyl]N'-[3-(methylthio)phenyl]urea. The methoxymethyl hydroxy protecting group was then removed, substantially in accordance with the procedure described in Example 6B, to provide 444 mg of title compound. m.p. 133°–138° C. (dec).

NMR(CDCl$_3$): $\delta = 1.43$ (s, 18H); 2.45(s, 3H); 4.34 (s, 2H); 5.25 (bs, 1H); 6.94–7.27 (m, CH).

Analysis for C$_{23}$H$_{32}$N$_2$O$_2$S:

Calculated: C, 68.96; H, 8.05; N, 6.79;
Found: C, 68.56; H, 7.87; N, 6.77.

EXAMPLE 12

N-[4-(Methylthio)phenyl]-4-nitrophenylcarbamate 4-(Methylmercapto)aniline (10.37 g; 74.6 mmol) and triethylamine (7.5 g; 74.6 mmol) were dissolved in 300 ml of tetrahydrofuran. To the resulting solution was slowly added (over a period of 5 minutes a solution of 15 g (74.6 mmol) of 4-nitrophenyl chloroformate dissolved in 50 ml of tetrahydrofuran. The resulting suspension was stirred for 30 minutes and then filtered. The filtrate was concentrated to dryness to provide 24.0 g of impure title product. This product was purified by trituration with toluene to provide 22.6 g of essentially pure title product.

EXAMPLE 13

N-[[3-(methylthiophenyl)-4-hydroxy-5-(1,1-dimethylethyl)phenyl]methyl]-N'-[4-(methylthio)phenyl]urea A. N-[3-(methylthiophenyl)-4-(methoxymethoxy)-5-[1,1-dimethylethyl)phenyl)methyl]-N'-[4-(methylthio)-phenyl]urea To a solution of 4.2 g (12.2 mmol) of the compound of Example 3 dissolved in 50 ml of toluene were added 3.70 g (12.2 mmol) of the compound of Example 12. The resulting solution was heated to reflux, stirred at that temperature for 45 minutes and then cooled to room temperature. Any solid particulates which had precipitated upon cooling were removed by filtration and the filtrate was concentrated to dryness to provide a residue. This residue was purified by column chromatography (10–40% ethyl acetate in hexane gradient as eluent) and fractions containing the desired product were combined and concentrated to dryness to provide 3.33 g of title compound.

B. N-[[3-(methylthiophenyl)-4-hydroxy-5-(1,1-dimethylethyl)phenyl]methyl]-N'-[4-(methylthio)phenyl]urea The compound prepared in Example 13A, above, (3.12 g; 6.1 mmol) was converted to title compound substantially in accordance with the procedures described in Example 6B. Such reaction provided 1.95 g of title compound. m.p. 132° C. (dec).

NMR(CDCl$_3$): δ=1.22 (s, 9H); 2.47 (s, 3H); 4.11 (s, 2H); 4.25 (s, 2H), 6.80–7.35 (m, 11H).

Analysis for C$_{26}$H$_{30}$N$_2$O$_2$S$_2$:

Calculated: C, 66.92; H, 6.48; N, 6.00;
Found: C, 67.00; H, 6.51; N, 6.00;

As noted previously, the compounds of the present invention are useful for preventing the development of diabetic complications in mammals suffering from diabetes. Such physiological activity was demonstrated in the following test systems.

Collagenase and stromelysin are matrix metalloendoproteases which are known to be synthesized and secreted by a number of cell types in response to Protein Kinase C (PKC) activation. Matrix metalloendoproteases are responsible for the degradation of extracellular matrix molecules in the basement membrane and play a role in cell invasiveness, tissue remodeling alterations in the microvasculature (increased capillary permeability and uncontrolled cell growth) and normal matrix turnover. Alterations in the microvasculature are hallmarks of diabetic complications such as kidney failure, blindness and neuropathy. Accordingly, the ability to modulate PKC driven pathways, such as the synthesis and secretion of the PKC enzyme precursor, procollagenase, should provide pharmacological advantages in treating diabetic complications.

The compounds of the present invention were evaluated for their ability to antagonize Protein Kinase C mediated procollagenase synthesis and secretion according to the following methodology.

Stimulation of the enzyme Protein Kinase C with 4-β-phorbol-12,13-dibutyrate (PDBu) leads human fibroblasts and other cells of endodermal, mesodermal and ectodermal origin to synthesize and secrete the enzyme precursor procollagenase. The stimulation of Protein kinase C, and the subsequent synthesis and release of procollagenase, occurs in a PDBu dose-dependent manner. Accordingly, a cell culture of primary human dermal fibroblasts was grown by seeding primary human dermal fibroblasts between passage numbers 5–15 into 96 well cell plates and then allowing such fibroblasts to grow to confluence using Dulbecco's Modified Eagles Medium (DME) supplemented with 4 mM glutamine and 10% fetal bovine serum (FBS) in a humidified 95/5 air/carbon dioxide incubator kept at 37° C. After the cells had reached confluence they were treated with 10 nM PDBu and test compounds for 72 hours using DME supplemented with FBS. A portion of the medium was removed for determination of collagenase activity using the following assay:

1. To each well of a round bottom, 96 well plate were added 50 µl of conditioned medium; 50 µl of a 5 µg/ml solution of collagenase substrate (N $^\alpha$-Biotin—Pro—Gln—Gly—Ile—Ala—Gly—D—Arg—Lys(-Ne—FITC)—OH) in a buffer composed of 100 mM HEPES [4-(2-hydroxyethyl)-1-piperazine-ethanesulfonic acid], 100 mM TAPS (3-{[tris(hydroxymethyl)-methyl]amino}-1-propanesulfonic acid, 10 mM calcium acetate and 1.0 mg/ml bovine serum albumin (BSA); and 50 µl of a 1.5 mM solution of 4-aminophenylmercuric acetate in the same HEPES/TAPS/calcium acetate/BSA buffer.

2. The well plate was incubated at 37° C. for 16 hours in a humidified incubator.

3. After 16 hours 20 µl of fluid from each well of the 96 well reaction plate were transferred to a new 96 well plate.

4. The transferred solutions were diluted with 180 µl of a buffer composed of 100 mM Tris-HCl, 100 mM EDTA; and 1 mg/ml BSA.

5. The well plate was incubated at room temperature for 30 minutes.

6. Twenty-five microliters of a 0.1% solution of Fluoricon Avidin Assay Particles (Pandex #31-040-1; Avidin conjugated to solid polystyrene beads 0.6–0.8 microns in diameter) in a buffer comprised of 0.02 M Tris [tris(hydroxymethyl)amino methane], 0.15 M sodium chloride and 1.0 mg/ml BSA were added to each well of a Pandex well plate.

7. Twenty-five microliters of the diluted reaction solution obtained after step 5, above, were added to each well of the well plate in step 6, above, and the resulting solution was mixed.

8. The Pandex well plate was loaded into a Pandex machine and the wells were washed with the buffer described in step 6.

9. After washing, the plates were read.

The results from the procedure described above are set forth in Table I, below. In Table I, column 1 provides the Example Number of the test compound employed. Column 2 provides the percentage of FBS used to supplement the DME solution. Finally, Column 3 provides the amount of test compound, in micrograms, required to obtain a 50% inhibition in the synthesis and secretion of procollagenase from human dermal fibroblasts.

TABLE I

| In Vitro Inhibition of Procollagenase | | |
|---|---|---|
| Test Compound Example No. | % FBS Used to Supplement DME | $IC_{50}$ ($\mu g$) |
| 6 | 1.0 | 2.3 |
| 6 | 1.0 | 1.5 |
| 6 | 1.0 | 0.7 |
| 6 | 2.0 | 3.2 |
| 7 | 1.0 | 2.3 |
| 7 | 1.0 | 1.9 |
| 7 | 2.0 | 2.4 |
| 7 | 1.0 | 1.7 |
| 8 | 1.0 | 5.0 |
| 9 | 1.0 | 2.1 |
| 10 | 1.0 | 5.0 |
| 10 | 1.0 | 3.7 |
| 11 | 1.0 | 5.0 |
| 13 | 2.0 | 8.6 |

The data provided in Table I, above, establish that the compounds of the present invention are efficacious in preventing the development of diabetic complications in mammals suffering from diabetes. To confirm such in vitro data, an in vivo experiment was conducted utilizing the rat chamber experimental methodology described in Williamson et al., *Diabetes*, 38, 1258 (1989) and Williamson, et al., *J. Clin. Invest.*, 85, 1167 (1990). Under this methodology, a chamber placed on the back of a rat mimics the diabetic state by creating high blood glucose levels. Creation of such high levels causes increased blood flow and increased permeability of blood vessels. Test compounds are administered to the rat at the same time the chamber is placed on the rat's back. Compound efficacy is then determined by comparing the blood flow rate and blood vessel permeability before and after the chamber is placed on the rat's back in order to determine to what extend the compound can prevent the increase in blood flow and vessel permeability.

The results from the rat chamber in vivo test system described above are set forth in Table II, below. In Table II, Column 1, provides the Example Number of the test compound employed, while Column 2 provides the concentration of active ingredient administered to the test animal. Finally, Column 3 provides the results obtained from the experiment as percent normalization of the diabetic state back to control for both blood vessel permeability and blood flow. Such results were calculated according to the following formula:

$$\% \text{ Normalization} = \frac{(PHGL - PC) - (PTC - PC)}{PHGL - PC} \times 100$$

PHGL = permeability of blood vessels (or blood flow) at high glucose levels (chamber on rat's back).
PC = permeability of blood vessels (or blood flow) at control state (prior to placing chamber on rat's back).
PTC = permeability of blood vessels (or blood flow) after test compound administered.

TABLE II

| In Vivo Rat Chamber Study | | | |
|---|---|---|---|
| Test Compound Example No. | Conc. of Test Compound $\mu m$ | % Normalization of Diabetic State | |
| | | Blood Vessel Permeability | Blood Flow |
| 6 | 20 | 66.12 | 35.48 |
| 7 | 20 | 59.24 | 49.70 |
| 7 | 20 | 102.18 | 64.51 |
| 9 | 20 | 8.45 | 23.29 |
| 10 | 20 | 1.99 | 17.56 |
| 11 | 20 | −30.34 | 21.50 |

As confirmation of the in vivo results obtained above, a second in vivo experiment was conducted. In this in vivo test system the compound of Example 7 was fed to diabetic rats at 0.1% of the rat's diet for seven weeks. After seven weeks the rats were killed and vascular permeability in a number of different organ systems was compared. The results obtained from such in vivo test system are set forth in Table III, below. In Table III, Column 1 discloses the organ system examined, while Columns 2, 3 and 4 disclose the vascular permeability in $\mu g$ of plasma/gram wet weight/minute for control (non-diabetic rats), untreated (diabetic rats/untreated) and treated (diabetic rats/treated), respectively (eight rats per each group).

TABLE III

| In Vivo Vascular Permeability Study | | | |
|---|---|---|---|
| Organ System | Control | Untreated | Treated |
| ocular anterior uvea | 254 ± 22[a] | 560 ± 119 | 373 ± 105 |
| ocular posterior uvea | 270 ± 68 | 563 ± 74 | 323 ± 91 |
| retina | 53 ± 15 | 162 ± 22 | 62 ± 18 |
| sciatic nerve | 59 ± 5 | 157 ± 45 | 59 ± 18 |
| aorta | 63 ± 22 | 261 ± 115 | 109 ± 65 |
| muscle | 44 ± 17 | 71 ± 28 | 59 ± 13 |
| brain | 29 ± 15 | 23 ± 11 | 26 ± 11 |
| heart | 580 ± 100 | 543 ± 63 | 547 ± 181 |
| kidney | 816 ± 128 | 1808 ± 1540 | 1208 ± 293 |

[a]Mean ± SD. $\mu g$ plasma/g wet weight/min.

The data in Tables I, II and III establish that the compounds of Formula I can be used to prevent the development of diabetic complications in mammals suffering from diabetes. Accordingly, the compounds of Formula I can be used to prevent the occurrence, or slow the onset of, atherosclerosis, kidney failure, retinopathy, nephropathy, neuropathy (and other complications commonly associated with diabetes) in a patient suffering from diabetes.

As discussed above, the compounds of Formula I are physiologically active thereby lending themselves to the valuable therapeutic method claimed herein. This method comprises administering to a mammal, preferably a human, suffering from or susceptible to one or more complications commonly associated with diabetes a sufficient amount of one or more of the compounds of Formula I so as to achieve the therapeutic or prophylactic intervention desired. The compounds can be administered by a variety of routes including the oral, rectal, transdermal, subcutaneous, intravenous, intramuscular or intranasal routes. The oral and transdermal routes of administration are preferred. No matter what route of administration is chosen, such administration is accomplished by means of pharmaceutical compositions which are prepared by techniques well known in the pharmaceutical sciences.

The method of the present invention encompasses preventing the development of diabetic complications in a prophylactic manner (i.e., using the compounds of Formula I to prevent the development of diabetic complications in a mammal susceptible to such complications before the complications actually occur or reoccur). Such prophylactic method of administration may be especially appropriate for elderly or heavy people since such individuals are particularly prone to diabetes and the complications associated therewith.

As mentioned above, the method of the present invention utilizes pharmaceutical compositions. Accordingly, the present invention is also directed to pharmaceutical compositions which include at least one compound of the present invention in association with one or more pharmaceutically acceptable carriers, diluents or excipients therefor.

In making the pharmaceutical compositions of the present invention, one or more active ingredients will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methylcellulose, methyl and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide rapid, sustained or delayed release of the active ingredient after administration to the patient by employing procedures well known in the art.

The compositions are formulated, preferably in a unit dosage form, such that each dosage contains from about 5 to about 500 mg, more usually about 25 to about 300 mg, of the active ingredient. The term "unit dosage form" refers to physically discrete units suitable as unitary dosages for human subjects and other mammals, each unit containing a predetermined quantity of active material calculated to produce the desired therapeutic or prophylactic effect, in association with one or more suitable pharmaceutical diluents, excipients or carriers.

The compounds of the present invention are effective over a wide dosage range for the indication for which they are administered. Thus, as used herein, the terms "effective amount" or "sufficient amount" refer to a dosage range of from about 0.5 to about 200 mg/kg of body weight per day. In the treatment of adult humans, the range of about 1 to about 50 mg/kg, in single or divided doses, is preferred. However, it will be understood that the amount of the compound actually administered will be determined by a physician, in the light of the relevant circumstances including the choice of compound to be administered, the chosen route of administration, the age, weight, and response of the individual patient, and the severity of the patient's symptoms and, therefore, the above dosage ranges are not intended to limit the scope of the invention in any way.

The following formulation examples may employ as active ingredients any of the compounds of Formula I. The examples are illustrative only and are not intended to limit the scope of the invention in any way.

EXAMPLE 15

Hard gelatin capsules are prepared using the following ingredients:

|  | Quantity (mg/capsule) |
| --- | --- |
| Compound of Example 7 | 250 |
| Starch dried | 200 |
| Magnesium stearate | 10 |

The above ingredients are mixed and filled into hard gelatin capsules in 460 mg quantities.

EXAMPLE 16

A tablet formula is prepared using the ingredients below:

|  | Quantity (mg/tablet) |
| --- | --- |
| Compound of Example 6 | 250 |
| Cellulose, microcrystalline | 400 |
| Silicon dioxide, fumed | 10 |
| Stearic acid | 5 |

The components are blended and compressed to form tablets each weighing 665 mg.

EXAMPLE 17

An aerosol solution is prepared containing the following components:

|  | Weight % |
| --- | --- |
| Compound of Example 9 | 0.25 |
| Ethanol | 29.75 |
| Propellant 22 (Chlorodifluoromethane) | 70.00 |

The active compound is mixed with ethanol and the mixture added to a portion of the propellant 22, cooled to $-30°$ C. and transferred to a filling device. The required amount is then fed to a stainless steel container and diluted with the remainder of the propellant. The valve units are then fitted to the container.

EXAMPLE 18

Tablets each containing 60 mg of active ingredient are made up as follows:

| Compound of Example 13 | 60 mg |
| --- | --- |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°-60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed by a tablet machine to yield tablets each weighing 150 mg.

EXAMPLE 19

Capsules each containing 80 mg of medicament are made as follows:

| | |
|---|---|
| Compound of Example 7 | 80 mg |
| Starch | 59 mg |
| Microcrystalline cellulose | 59 mg |
| Magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

EXAMPLE 20

Suppositories each containing 225 mg of active ingredient are made as follows:

| | |
|---|---|
| Compound of Example 10 | 225 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

EXAMPLE 21

Suspensions each containing 50 mg of medicament per 5 ml dose are made as follows:

| | |
|---|---|
| Compound of Example 13 | 50 mg |
| Sodium carboxymethylcellulose | 50 mg |
| Syrup | 1.25 ml |
| Benzoic acid solution | 0.10 ml |
| Flavor | q.v. |
| Color | q.v. |
| Purified water to | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

EXAMPLE 22

Capsules each containing 150 mg of medicament are made as follows:

| | |
|---|---|
| Compound of Example 6 | 150 mg |

| -continued | |
|---|---|
| Starch | 164 mg |
| Microcrystalline cellulose | 164 mg |
| Magnesium stearate | 22 mg |
| Total | 500 mg |

The active ingredient, cellulose, starch and magnesium stearate are blended, passed through a No. 45 mesh U.S. sieve, and filled into hard gelatin capsules in 500 mg quantities.

We claim:

1. A method for preventing the development of diabetic complications selected from kidney failure, retinopathy, nephropathy and neuropathy in mammals comprising administering to a mammal in need of such prevention an effective amount of a compound of the formula.

$$\underset{RO}{\overset{R^1}{\underset{R^2}{\text{Ar}}}} (CH_2)_n - \underset{R^3}{\overset{X}{\underset{|}{N}}} - \overset{\|}{C} - \underset{R^5}{\overset{|}{N}} - (CH_2)_m - Y$$

wherein:

R is hydrogen, $C_1$-$C_8$ alkyl, $C_3$-$C_8$ cycloalkyl, $C_1$-$C_6$ alkylphenyl or a hydroxy protecting group;

$R^1$ and $R^2$ are each independently hydrogen, $C_1$-$C_6$ alkyl, $C_3$-$C_8$ cycloalkyl, $C_1$-$C_6$ alkoxy, $C_2$-$C_6$ alkenyl, $C_2$-$C_6$ alkynyl, $S(O)q(C_1$-$C_6$ alkyl) or $$-(CH_2)_p - A - \underset{W^1}{\overset{W^2}{\text{Ar}}};$$

A is $-CH_2-$, $-O-$, $-S-$, $-S(O)-$ or $-S(O_2)-$:

$W^1$ and $W^2$ are each independently hydrogen, halo, hydroxy, $C_1$-$C_4$ alkyl, $C_1$-$C_4$ alkoxy, $C_1$-$C_4$ alkylthio, $C_2$-$C_4$ alkenyl or $C_2$-$C_4$ alkynyl;

$R^3$ is hydrogen, $C_1$-$C_8$ alkyl, $C_3$-$C_8$ cycloalkyl or $C_1$-$C_6$ alkylphenyl;

X is O, S or $NR^4$;

$R^4$ is hydrogen, $C_1$-$C_6$ alkyl, $C_1$-$C_4$ alkylphenyl or $C_1$-$C_6$ alkoxy;

$R^5$ is hydrogen, $C_3$-$C_8$ cycloalkyl or $C_1$-$C_8$ alkyl;

Y is

[structures: phenyl with $Z^2$, $Z^1$; naphthyl with $Z^1$, $Z^2$; benzothiophene (S); benzofuran (O)]

$Z^1$ and $Z^2$ are each independently hydrogen, $C_1$–$C_6$ alkyl, $C_3$–$C_8$ cycloalkyl, $C_1$–$C_6$ alkoxy, hydroxy, $C_2$–$C_6$ alkenyl, $C_2$–$C_6$ alkynyl, $C_1$–$C_6$ alkylthio, halo, trifluoromethyl or —$NR^6R^7$;

$R^6$ and $R^7$ are each independently hydrogen, $C_3$–$C_8$ cycloalkyl, $C_1$–$C_6$ alkyl or $C_1$–$C_4$ alkylphenyl;

n is 1 to 5, both inclusive;

m and p are each independently 0 to 6, both inclusive;

q is 0, 1 or 2; and pharmaceutically acceptable salts thereof.

2. A method as claimed in claim 1 wherein R is hydrogen, $C_1$–$C_8$ alkyl, $C_3$–$C_8$ cycloalkyl or $C_1$–$C_6$ alkylphenyl.

3. A method as claimed in claim 2 wherein X is O or S.

4. A method as claimed in claim 3 wherein n is 1 or 2 and m is 0, 1 or 2.

5. A method as claimed in claim 4 wherein n is 1 and m is 0.

6. A method as claimed in claim 5 wherein Y is

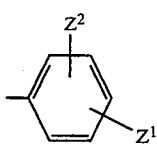

wherein:

$Z^1$ and $Z^2$ are each independently hydrogen, $C_1$–$C_6$ alkyl, $C_3$–$C_8$ cycloalkyl, $C_1$–$C_6$ alkoxy, hydroxy, $C_2$–$C_6$ alkenyl, $C_2$–$C_6$ alkynyl, $C_1$–$C_6$ alkylthio, halo, trifluoromethyl or —$NR^6R^7$.

7. A method as claimed in claim 6 wherein $R^3$ and $R^5$ are each independently hydrogen or methyl.

8. A method as claimed in claim 7 wherein $R^3$ and $R^5$ are both hydrogen.

9. A method as claimed in claim 8 wherein $R^1$ and $R^2$ are each independently $C_1$–$C_6$ alkyl, $C_1$–$C_6$ alkoxy, $C_1$–$C_6$ alkylthio or $C_1$–$C_4$ alkylthiophenyl.

10. A method as claimed in claim 9 wherein Y is

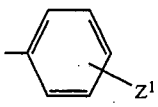

wherein $Z^1$ is hydrogen, $C_1$–$C_4$ alkyl, $C_1$–$C_6$ alkoxy or $C_1$–$C_6$ alkylthio.

11. A method as claimed in claim 10 wherein R is hydrogen or $C_1$–$C_4$ alkyl.

12. A method as claimed in claim 11 wherein R is hydrogen or methyl; $R^1$ and $R^2$ are each independently n-propyl, isopropyl, n-butyl, sec-butyl, t-butyl, methoxy, ethoxy, methylthio, ethylthio, methylthiophenyl or ethylthiophenyl and Y is

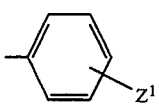

wherein $Z^1$ is hydrogen, methyl, ethyl, methoxy, ethoxy, methylthio or ethylthio.

13. A method as claimed in claim 12 in which the compound is N-[[3,5-bis(1,1-dimethylethyl)-4-hydroxyphenyl]methyl N'-[4-(methylthio)phenyl]urea or a pharmaceutically acceptable salt thereof.

14. A method as claimed in claim 12 in which the compound is N-[[3,5-bis(1,1-dimethylethyl)-4-methoxyphenyl]methyl]-N'-(4-methylthio)phenyl]urea or a pharmaceutically acceptable salt thereof.

15. A method as claimed in claim 12 in which the compound is N-[[3,5-bis(1,1-dimethylethyl)-4-hydroxyphenyl]methyl]-N'-[2-(methylthio)phenyl]urea or a pharmaceutically acceptable salt thereof.

16. A method as claimed in claim 12 in which the compound is N-[[3,5-bis(1,1-dimethylethyl)-4-hydroxyphenyl]methyl]-N'-phenylthiourea or a pharmaceutically acceptable salt thereof.

17. A method as claimed in claim 12 in which the compound is N-[[3,5-Bis(1,1-dimethylethyl) hydroxyphenyl]methyl]-N'-phenyl urea or a pharmaceutically acceptable salt thereof.

18. A method as claimed in claim 12 in which the compound is N-[[3,5-bis(1,1-dimethylethyl) -4-hydroxyphenyl]methyl-N'-3-(methylthio)phenyl]urea or a pharmaceutically acceptable salt thereof.

* * * * *

UNITED STATES PATENT AND TRADEMARK OFFICE
CERTIFICATE OF CORRECTION

PATENT NO. : 5,441,984
DATED : August 15, 1995
INVENTOR(S) : William F. Heath, JR. Jill A. Panetta, John K. Shadle It is certified that error appears in the above-indentified patent and that said Letters Patent is hereby corrected as shown below:

Column 28, line 27 should read

"phenyl]methyl]-N'-[4-(methylthio)phenyl]urea or a phar-"

Column 28, line 42 should read

"compound is N-[[3,5-Bis(1,1-dimethylethyl)-4-hydroxy-"

Column 28, line 47 should read

"phenyl]methyl-N'-[3-(methylthio)phenyl]urea or a phar-"

Signed and Sealed this

Twenty-first Day of November, 1995

Attest:

BRUCE LEHMAN

Attesting Officer

Commissioner of Patents and Trademarks